United States Patent
Frick et al.

(10) Patent No.: US 6,871,828 B2
(45) Date of Patent: Mar. 29, 2005

(54) STAND FOR A SURGICAL MICROSCOPE

(75) Inventors: Roman Frick, Steinteilweg (AT); Andrzej Metelski, Spielgasse (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 10/603,506

(22) Filed: Jun. 25, 2003

(65) Prior Publication Data

US 2004/0104327 A1 Jun. 3, 2004

(30) Foreign Application Priority Data

Dec. 3, 2002 (DE) .................................. 202 18 691 U

(51) Int. Cl.[7] .............................................. F16M 13/00
(52) U.S. Cl. ..................... 248/415; 248/125.7; 248/324
(58) Field of Search ............................... 248/415, 121, 248/122.1, 125.7, 125.9, 317, 324, 338

(56) References Cited

U.S. PATENT DOCUMENTS 6,364,268 B1 * 4/2002 Metelski ..................... 248/317
6,522,748 B1 * 2/2003 Wang ........................... 379/446
2002/0185583 A1 * 12/2002 Metelski ..................... 248/676

FOREIGN PATENT DOCUMENTS

DE        102 23 166 A1    12/2002

* cited by examiner

Primary Examiner—Korie Chan
(74) Attorney, Agent, or Firm—Hodgson Russ LLP

(57) ABSTRACT

The invention concerns a stand (1) for a surgical microscope, having a stand column (2) and having at least one pivot arm (3). The pivot arm (3) is arranged pivotably about a vertical rotation axis (5) by way of a rotary bearing (4). A tilting device (6) for adjustably tilting the rotation axis relative to the column is provided, wherein the tilting device (6) includes a bearing shaft (8) supported by the column and defining a substantially horizontal tilting axis, and an adjustment housing (7) mounted on the bearing shaft (8) for rotation about the tilting axis. The rotary bearing (4) is carried by the adjustment housing (7).

6 Claims, 2 Drawing Sheets

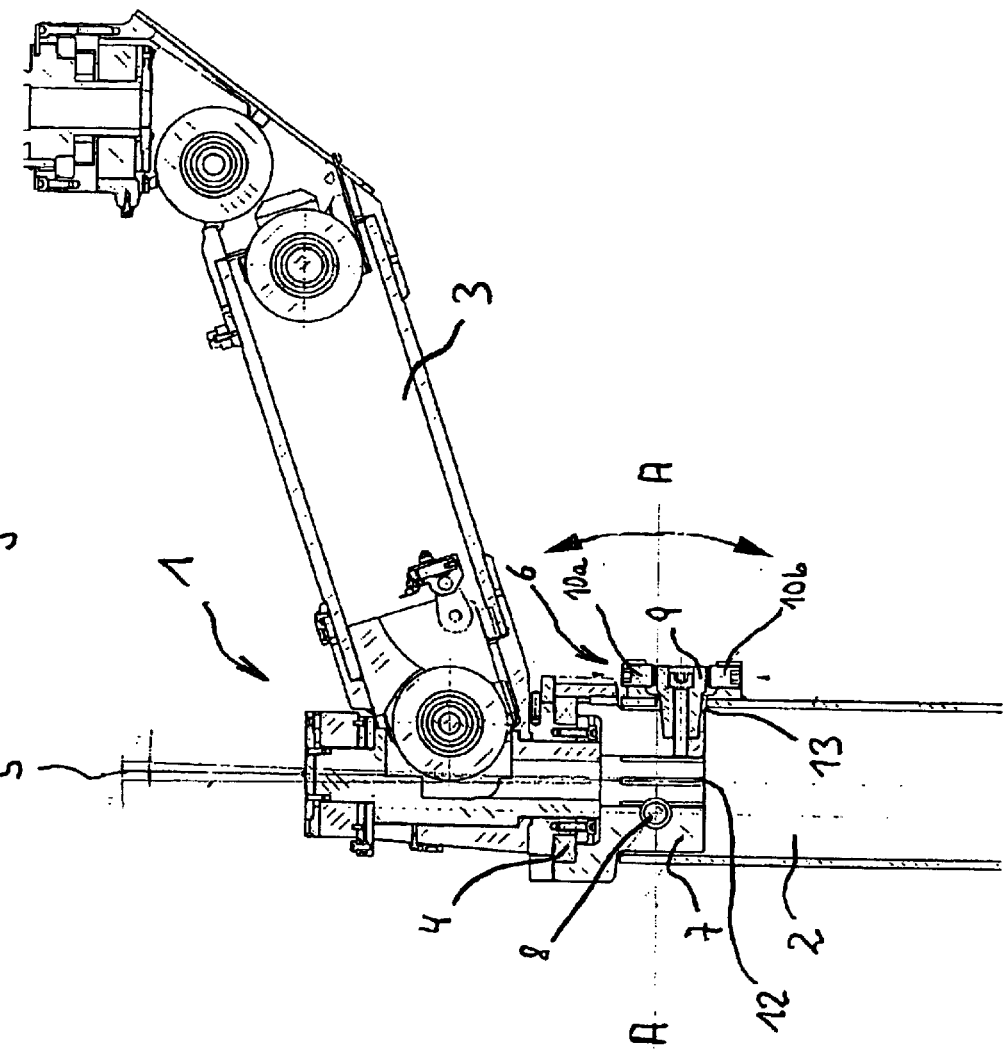

ically as the invention.

STAND FOR A SURGICAL MICROSCOPE

CROSS REFERENCE TO RELATED APPLICATIONS

This application claims priority of the German utility model application 202 18 691.1 filed Dec. 3, 2002 which is incorporated by reference herein.

FIELD OF THE INVENTION

The invention concerns a stand for a surgical microscope of the type having a column and a pivot arm mounted on the column by a rotary bearing.

BACKGROUND OF THE INVENTION

The purpose of such stands is to hold a relatively heavy microscope for an operator so that it is movable as smoothly as possible. The joints or bearings need to be made as resistance-free as possible so as to present the user with as little resistance as possible when moving the stand or the stand arms.

If these stands are positioned on uneven floors or if torques on the stand occur as a result of changes in loads, the relevant moving parts of the stand, in particular the stand arm, exhibit a drift behavior in the unbraked state. "Drift behavior" is to be understood as lateral pivoting motions about a rotation axis, or tendencies toward such pivoting motions, by the carrier arm, which are undesirable for the user.

Drift can occur with ceiling mounts as well. It results whenever deflections occur as a result of limited rigidity of one of the horizontal stand arms, and further horizontally arranged arms or components are pivotably mounted on that stand arm.

In surgical microscopes, drifting of the stand arms about an axis is prevented by way of an electromagnetic brake. When this brake is released, however, in order to displace the stand or the microscope arranged on the stand, the moving parts of the stand can drift and the operator must exert a corresponding amount of force in order to stop that drift.

A stand for a surgical microscope having an electromagnetic brake is known from DE 101 23 166 A1. In order to optimize drift behavior when the brake is released, provision is made in the context of this stand for each individual pivot axis automatically to be held perpendicular by way of a complex mechanism. This mechanism has proven successful in practice, but its production is complex and correspondingly expensive. Especially in the case of stands for surgical microscopes which, because of their utilization, are pivoted over only very small ranges (as is the case, for example, with stands for ophthalmology), lesser requirements are imposed in terms of absence of drift in the stand.

Undesirable drifting behavior may also occur upon assembly of a stand of this kind, caused by small production tolerances of individual components. Complex alignments are then necessary upon assembly in order to compensate for or minimize that drifting behavior.

SUMMARY OF THE INVENTION

It is therefore the object of the invention to prevent, with simple means, the drift of a stand resulting from production tolerances.

The invention is characterized in that an adjustment housing having a tilting device is provided, with which the rotation axis for the pivot arm is modifiable as to its position. Drifting of the pivot arm is thereby prevented.

In a further embodiment of the invention, the adjustment housing is joined rigidly to a trunnion, or the trunnion is shaped directly onto the adjustment housing.

In a development of the invention, the adjustment housing is arranged on or in the stand column.

In a further embodiment, the invention is also characterized in that the adjustment housing has two adjusting screws, arranged opposite one another, of which the one is embodied as an adjusting screw and the other as a locking screw. The result of this is that once an alignment has been made, it can be fixed in place.

In a development of the invention, the adjusting screws are arranged parallel to the vertical rotation axis or parallel to the stand column.

In a further embodiment of the invention, the trunnion is guided between the two adjusting screws. The result of this is that the trunnion can be raised or lowered by the adjusting screw, and after the adjustment, the position of the trunnion and thus the position of the vertical rotation axis can be fixed by way of the locking screw.

In a development of the invention, the vertical rotation axis is embodied to be adjustable by +/−2 degrees by way of the tilting device. This small change in position is sufficient to compensate for production tolerances that occur.

In a further embodiment of the invention, the stand is embodied either as a floor stand or a ceiling mount.

BRIEF DESCRIPTION OF THE DRAWINGS

The invention will be depicted and described in an exemplary embodiment with reference to the schematic drawings, in which:

FIG. 2 shows a section through the stand column of the stand and the pivot arm.

DETAILED DESCRIPTION OF THE INVENTION

Figure 1:
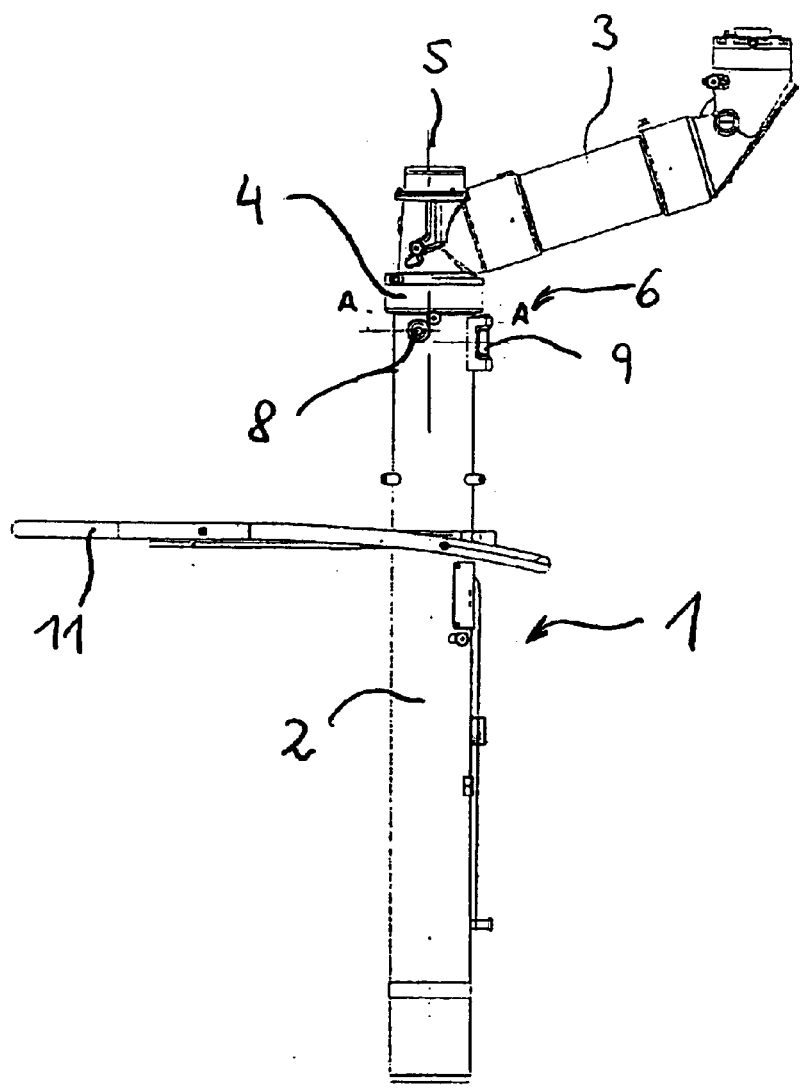
FIG. 1 is a partial view of the stand.

FIG. 1 shows a stand 1 for a surgical microscope (not depicted), having a stand column 2 and a pivot arm 3. A bracket 11 for moving the entire stand 1 is arranged on stand column 2. Either stand column 2 is equipped with a stand foot with which stand 1 can be unrestrictedly positioned in space, or stand column 2 is attached via a receptacle to the ceiling of an operating room.

Stand column 2 has a vertical rotation axis 5 about which pivot arm 3 is embodied movably. For that purpose, stand column 2 has a rotary bearing 4.

Also associated with stand column 2 is a tilting device 6 having a bearing shaft 8 with respect to which the vertical rotation axis 5 is displaceable. Tilting device 6 is equipped for that purpose with a trunnion 9.

FIG. 2 shows a section through stand 1 in the region of rotary bearing 4. Stand column 2 has an adjustment housing 7 having a bearing shaft 8. By way of bearing shaft 8, adjustment housing 7 is tiltable with respect to stand column 2 and with respect to the vertical axis of column 2. Adjustment housing 7 carries a rotary bearing 4 by means of which pivot arm 3 is mounted pivotably about vertical rotation axis 5. Pivot arm 3 is joined to adjustment housing 7 via rotary bearing 4.

Immovably joined to adjustment housing 7 is a trunnion 9 that extends out from the interior of stand column 2 via a bore 13.

Arranged on stand column 2 are two adjusting screws 10*a*, 10*b*, located opposite one another, between which trunnion 9 is mounted.

Rotation of adjusting screw 10*b* causes adjustment housing 7 to be pivoted about bearing axis 8, thus modifying the position of vertical rotation axis 5 and pivot arm 3.

After the change in position of rotation axis 5, the position of rotation axis 5 is fixed by locking adjusting screw 10*b* using the opposite adjusting screw 10*a*.

Figure 3:
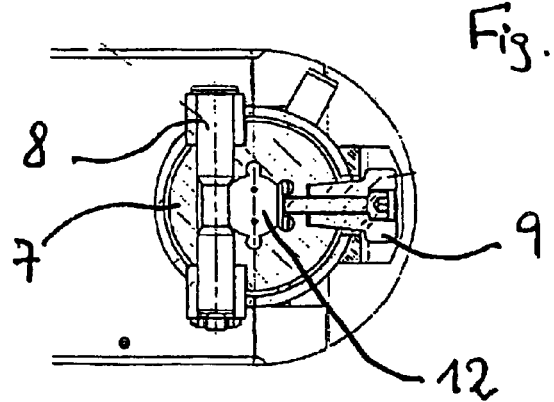
FIG. 3 shows a section through the adjustment housing along line A—A of FIG. 2.

FIG. 3 shows a section through rotary bearing 4 along line A—A of FIG. 2, with adjustment housing 7, bearing shaft 8, and trunnion 9. Adjustment housing 7 is equipped in its core with a cable conduit 12 for receiving cables and/or conductors.

Parts List
1 Stand
2 Stand column
3 Pivot arm
4 Rotary bearing
5 Vertical rotation axis
6 Tilting device
7 Adjustment housing
8 Bearing shaft
9 Trunnion
10*a* Adjusting screw
10*b* Adjusting screw
11 Bracket
12 Cable conduit
13 Bore

What is claimed is:

1. An apparatus (1) for a surgical microscope comprising:

a column (2);

a pivot arm (3);

a rotary bearing (4) mounting the pivot arm on the column for rotation about a substantially vertical rotation axis (5);

a tilting device (6) for tilting the rotation axis relative to the column, the tilting device (6) including a bearing shaft (8) supported by the column and defining a substantially horizontal tilting axis, and an adjustment housing (7) mounted on the bearing shaft (8) for rotation about said tilting axis; and a trunnion (9) fixed to said adjustment housing (7).

2. The apparatus (1) as defined in claim 1, wherein the adjustment housing (7) is arranged in the column (2).

3. An apparatus (1) for a surgical microscope comprising:

a column (2);

a pivot arm (3);

a rotary bearing (4) mounting the pivot arm on the column for rotation about a substantially vertical rotation axis (5);

a tilting device (6) for tilting the rotation axis relative to the column, the tilting device (6) including a bearing shaft (8) supported by the column and defining a substantially horizontal tilting axis, and an adjustment housing (7) mounted on the bearing shaft (8) for rotation about said tilting axis;

wherein the adjustment housing (7) is arranged in the column (2); and wherein the tilting device (6) further includes two adjusting screws (10*a*; 10*b*) arranged opposite one another and associated with the adjustment housing (7).

4. The apparatus (1) as defined in claim 3, wherein the adjusting screws (10*a*; 10*b*) extend parallel to the rotation axis (5).

5. The apparatus (1) as defined in claim 4, wherein a trunnion (9) is guided between the two adjusting screws (10*a*; 10*b*).

6. The apparatus (1) as defined in claim 3, wherein a trunnion (9) is guided between the two adjusting screws (10*a*; 10*b*).

* * * * *